(12) United States Patent
Leroy et al.

(10) Patent No.: US 11,026,639 B2
(45) Date of Patent: Jun. 8, 2021

(54) DEVICE FOR VISUALIZING AN INTERNAL ORGAN OF A PATIENT AND ASSOCIATED VISUALIZATION METHOD

(71) Applicant: KOELIS, Meylan (FR)

(72) Inventors: Antoine Leroy, Bois d'arcy (FR); Patrick Henri, Bois-Colombes (FR); Michael Baumann, Grenoble (FR); Eric Gaudard, Lyons (FR); Johan Sarrazin, St Martin d'Heres (FR)

(73) Assignee: KOELIS, Meylan (FR)

( * ) Notice: Subject to any disclaimer, the term of this patent is extended or adjusted under 35 U.S.C. 154(b) by 0 days.

(21) Appl. No.: 16/466,550

(22) PCT Filed: Dec. 7, 2017

(86) PCT No.: PCT/EP2017/081838
§ 371 (c)(1),
(2) Date: Jun. 4, 2019

(87) PCT Pub. No.: WO2018/104458
PCT Pub. Date: Jun. 14, 2018

(65) Prior Publication Data
US 2020/0077964 A1   Mar. 12, 2020

(30) Foreign Application Priority Data
Dec. 8, 2016   (FR) ..................................... 1662141

(51) Int. Cl.
*G06T 11/00*   (2006.01)
*A61B 5/00*   (2006.01)
(52) U.S. Cl.
CPC ............ *A61B 5/743* (2013.01); *A61B 5/7221* (2013.01); *G06T 11/001* (2013.01); *G06T 2210/41* (2013.01)

(58) Field of Classification Search
None
See application file for complete search history.

(56) References Cited

U.S. PATENT DOCUMENTS

| 2009/0093715 A1 | 4/2009 | Downey et al. |
| 2010/0172559 A1 | 7/2010 | Kumar et al. |
| 2014/0142422 A1 | 5/2014 | Manzke et al. |

OTHER PUBLICATIONS

Yiqiang Zhan et al., "Targeted Prostate Biopsy Using Statistical Image Analysis", IEEE Transactions on Medical Imaging, IEEE Service Center, Jun. 1, 2007, pp. 779-788, vol. 26, No. 6, Piscataway, NJ, US.

(Continued)

*Primary Examiner* — Nicholas R Wilson
(74) *Attorney, Agent, or Firm* — Sughrue Mion, PLLC

(57) ABSTRACT

The invention concerns a device for displaying an internal organ of a patient comprising a computer (2) and a screen (3) connected to the computer in order to display at least one image of the internal organ. According to the invention, the computer is arranged to determine, from at least one medical examination previously carried out on the internal organ, at least one confidence area (10) and/or at least one affected area (11), at least partially encompassing one or more portions (9) of the internal organ where samples have been taken and/or at least partially encompassing one or more areas previously identified as suspect during a medical imaging procedure, and to display, on the screen, the image of the internal organ supplemented with the confidence area and/or the affected area. The invention also concerns a corresponding display method.

20 Claims, 3 Drawing Sheets

(56) References Cited

OTHER PUBLICATIONS

International Search Report for PCT/EP2017/081838, dated May 20, 2018.

DEVICE FOR VISUALIZING AN INTERNAL ORGAN OF A PATIENT AND ASSOCIATED VISUALIZATION METHOD

This Application is a National Stage of International Application No. PCT/EP2017/081838 filed Dec. 7, 2017, claiming priority based on French Patent Application No. 16 62141 filed Dec. 8, 2016.

The invention relates to a device for visualizing an internal organ of a patient, and to an associated visualization method.

BACKGROUND OF THE INVENTION

At present, many diseases can only really be diagnosed by collecting and analyzing samples taken from the anatomical volume that is to be monitored. Possible examples include screening for diseases of the liver, prostate, kidneys, uterus or endometrium.

The standard procedure for detecting prostate cancer thus involves performing biopsies of the prostate. The diseased tissues affected by prostate cancer are generally indistinguishable from healthy tissues in conventional medical images of the ultrasound type. For their part, magnetic resonance imaging (MRI) and positron emission tomography (PET) are more sensitive and more specific to the pathology and sometimes make it possible to identify suspect lesions.

Grades have therefore been specifically developed to classify what are called "suspect zones" identified during these examinations. For magnetic resonance imaging, these include the PI-RADS scale (also called the ESUR Score), the Likert scale, etc. On the images resulting from these examinations, these suspect zones are represented, with the aid of detection algorithms, as semi-automatic detection contours, with possible manual adjustment by an expert such as a radiologist, or else are directly represented manually by the expert.

Most of the time, however, the scores attributed by the scale used are insufficient to be able to allow a diagnosis and therefore to replace the analysis of the samples obtained by biopsy.

In the case of the prostate, the biopsies can traditionally be performed by a transrectal approach or by a transperineal approach.

Transrectal biopsies are traditionally performed on an outpatient basis with local anesthesia, the procedure then taking less than an hour. However, transrectal biopsies may conceivably also be performed under general anesthesia. The patient is placed in a lateral decubitus position (on one side with the knees bent up toward the abdomen) or in a lithotomy position. Once the patient has been positioned, the urologist inserts an endorectal probe via the rectum of the patient, a guide needle being fixed to the probe in order to puncture the prostate via the rectum.

Transperineal biopsies are in most cases performed under general anesthesia. The patient is in a lithotomy position. As in the transrectal approach, an endorectal probe is inserted into the rectum of the patient in order to observe the prostate by ultrasound. However, a puncture guide is placed in front of the perineum of the patient (in front of the rectum and behind the genitals) in order to guide the biopsy needle, which will then pass through the skin of the perineum in order to reach the prostate.

In both cases, the clinician performs multiple biopsies, according to a systematic protocol, from the whole of the prostate, and/or a small number of biopsies concentrated on suspect regions that have been detected beforehand, for example in magnetic resonance images.

The document US 2009/093715 thus proposes a method for establishing a plan for performing biopsies of the prostate.

The document US 2010/0172559 proposes a method making it easier to visualize the prostate when planning biopsy procedures.

Following hisotological, chemical, genetic or molecular analysis of the collected samples, the clinician receives a report indicating the level of severity with which each sample is affected. The report sometimes also indicates the level of severity with which a particular anatomical zone is affected or with which the entirety of the organ is affected. If disease is confirmed, the results can thus help the clinician to characterize the disease and define the best possible management of the patient.

In order to assist the clinician in his analysis, various types of classification are known for quantifying the degree of severity of each sample.

For example, there is the TNM staging system, which is a classification with three criteria defining the state of the tumor, the state of the regional lymph nodes and distant metastases.

With this TNM staging system, prostate cancer can be classed under four different stages, such as:
localized prostate cancer,
locally advanced prostate cancer,
prostate cancer with involvement of the pelvic lymph nodes,
metastatic prostate cancer.

There is also the Gleason grading system which entails visual analysis of (microscopic) tissues and which grades cancer in five groups, where the aggressiveness increases in the direction of a group 5 score.

There is also the D'Amico classification which, on the basis of various scores cited above and on others, describes the localized forms of prostate cancer according to their possible evolution. There are three subgroups:
low-risk localized prostate cancer,
intermediate-risk prostate cancer,
high-risk prostate cancer.

There are also grading systems based on genomic tests, for example the tests marketed under the name Prolaris (trademark) by Myriad Genetics, Oncotype DX (trademark) by Genomic Health, or ConformMdx (trademark) by MdxHealth.

Finally, there are grading systems based on biomarkers (chemical, genetic, hormonal and imaging biomarkers, etc.) or on the basis of spectroscopic analyses (especially Raman spectroscopy, also called Raman spectrometry) of the samples collected.

Following the various examinations carried out, and in light of the report or reports received (indicating the level of severity with which each sample is affected and/or which zones are identified as suspect during an imaging procedure), the clinician then decides on the most appropriate way of managing the patient (taking into consideration the best benefit/risk ratio and the best possible quality of life for the patient). For example, he may decide only on periodic monitoring (also called active monitoring) of the development of the disease or, on the contrary, he may decide on a treatment (qualifying step).

If treatment is indicated, the following step then involves the clinician estimating the anatomical volume or volumes affected by the disease and thereafter delimiting one or more treatment volumes (delimiting step).

This step of delimiting the treatment volume represents a major difficulty for the clinician since, as regards biopsies, it is only the biopsy sites that have been examined. In addition, even if the clinician also has other information available to him from medical imaging, the suspect zones identified on these medical images often correspond only roughly to the volume actually affected by the disease.

Thus, even with all of this diagnostic information, the clinician is limited to forming a mental image of the general state of the prostate and of the patient in order to identify the zones which he considers healthy and those which he deems suspect, in order thereby to determine a treatment volume.

During this step of delimiting the disease and determining the treatment volume, the clinician is also required to identify critical structures which, as far as possible, have to be preserved during the treatment.

This may lead to situations of overtreatment if the clinician decides to overextend the treatment zone with a view to controlling the risks of recurrence. Conversely, if he underestimates the volume affected by the disease, the risk of recurrence is high.

In order to aid clinicians, the present applicant already offers a mapping system which permits a three-dimensional view of the prostate and of the locations where the various samples were taken from the prostate. It is also possible to display, in the same reference system as the above information, the suspect volumes detected by other medical examinations, for example by magnetic resonance imaging.

Such a mapping system is illustrated by way of example in FIG. 1.

Although this permits a better understanding of the situation, it is still difficult for the clinician to establish how far the cancer has developed in the prostate. It is therefore still possible for situations of undertreatment or overtreatment to arise. In the case of overtreatment, the clinician will carry out extensive treatment involving the entirety or at least one hemisphere of the prostate (by radical prostatectomy, radiotherapy, low-dose curietherapy, etc.). This poses major postoperative problems such as damage to the peripheral organs, pain, bleeding, loss of erectile function, incontinence, etc.).

In the case of undertreatment, there is a greater risk of recurrence, with possible worsening of the disease over time.

The document US 2014/0142422 proposes a system for guiding an instrument during an endoscopic operation.

OBJECT OF THE INVENTION

It is an aim of the invention to make available a device for visualizing an internal organ of a patient, limiting a risk of undertreatment or overtreatment of said internal organ. It is also an aim of the invention to make available a corresponding visualization method.

BRIEF DESCRIPTION OF THE INVENTION

To this end, the invention relates to a device for visualizing an internal organ of a patient, comprising a computer and a screen connected to the computer in order to display at least one image of the internal organ.

According to the invention, the computer is arranged
to determine, from at least one medical examination previously carried out on the internal organ, at least one confidence zone and/or at least one affected zone, at least partially encompassing one or more portions of the internal organ where samples have been taken and/or at least partially encompassing one or more zones previously identified as suspect during a medical imaging procedure, the determination being based on:
a statistical approach to the presence of healthy or diseased tissues around a portion of the internal organ where at least one sample has been taken and/or around an zone previously identified as suspect during the medical imaging procedure; and/or on an analysis of the samples taken;
to display, on the screen, the image of the internal organ supplemented with the confidence zone and/or the affected zone.

The clinician thus has available an image of the internal organ incorporating an affected zone and/or a confidence zone, taking account of the information acquired during the medical examination (which can involve biopsy or medical imaging such as radiological medical imaging, MRI, PET, etc.). The image displayed is not therefore limited, for example, to the representation of the various samples and/or simply to a medical image itself (for example of the MRI type) but to the tissues surrounding the various samples or a zone identified as suspect during the medical examination.

Since the medical examination is dedicated to the internal organ under consideration, and preferably dedicated to a localized and internal study of the organ under consideration, it is possible to tailor the confidence zone and/or affected zone to each patient, which allows the clinician to better estimate the appropriate treatment, for example.

It thus proves easier for a clinician to imagine the situation and the development of a disease, typically a cancer, within the internal organ. This in particular allows the clinician to better estimate, for example, the appropriate treatment (planning step).

For the present application, "confidence zone" signifies a zone of the internal organ that is healthy and free of any trace of disease, and "affected zone" signifies a zone of the internal organ that is already at least partially affected by the disease.

In particular, the computer is arranged to project a three-dimensional image of the internal organ on the screen.

In particular, the computer is arranged to project two-dimensional sectional images of the internal organ.

In particular, the computer is arranged to display, on the image of the internal organ, at least one portion of the internal organ that has been punctured during the sampling procedures.

In particular, the confidence zone and/or the affected zone completely encompasses said portion.

In particular, the confidence zone and/or the affected zone is displayed on the screen with a color gradient depending on the distance from the sampled portion and/or on the criticality of the disease possibly detected in said portion.

In particular, the confidence zone and the affected zone are not displayed in the same color.

In particular, the computer is configured in such a way as to display, on the image of the internal organ, at least one zone of the internal organ that is to be preserved.

In particular, the computer is additionally configured to partition the internal organ into different elements and to display, on the image of the internal organ, the partition formed by these different elements.

In particular, the confidence zone and/or the affected zone is formed by one or more elements.

In particular, the computer is configured in such a way as to display, on the image of the internal organ, at least one item of information associated with the confidence zone and/or the affected zone.

In particular, the computer is configured to be able to display a diseased general part encompassing at least some of the various affected zones.

In particular, the computer is configured in such a way as to partition the internal organ into different elements and to display, on the image of the internal organ, the partition formed by these various elements, the computer additionally being configured in such a way as to display a diseased general part encompassing at least one element of the partition comprising one or more affected zones.

In particular, the computer is configured in such a way that the diseased general part also encompasses at least one element of the partition in contact with the element of the partition comprising one or more affected zones.

In particular, the computer is configured to export the displayed image to an external peripheral.

In particular, the computer is arranged to define the affected zone and/or the confidence zone also with the aid of a measurement error of the apparatus that was involved in the medical examination performed beforehand on the internal organ.

The invention also relates to a method for visualizing an internal organ of a patient with the aid of a device as described, comprising the step of determining the one or more confidence zones and/or affected zones and of displaying said one or more zones.

Other features and advantages of the invention will become clear on reading the following description of particular non-limiting embodiments of the invention.

BRIEF DESCRIPTION OF THE DRAWINGS

The invention will be better understood on reading the following description of particular embodiments of the invention with reference to the attached figures, in which.

DETAILED DESCRIPTION OF THE INVENTION

Figure 1:
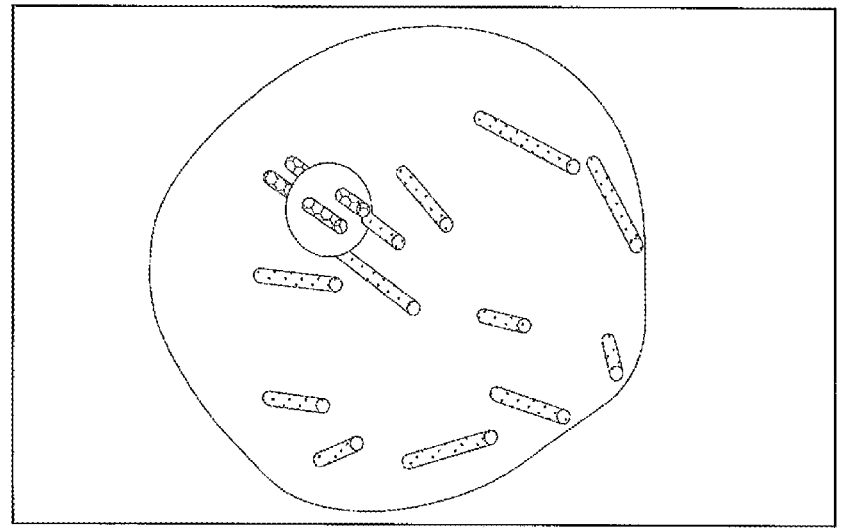
FIG. 1 shows a mapping system of the prior art.
Figure 2:
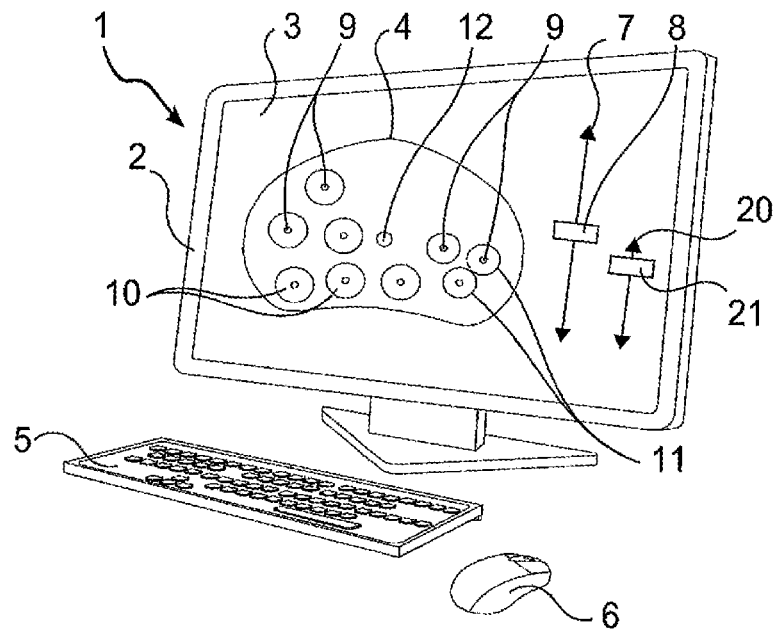
FIG. 2 is a schematic illustration of a display device according to a first embodiment of the invention.
Figure 3:
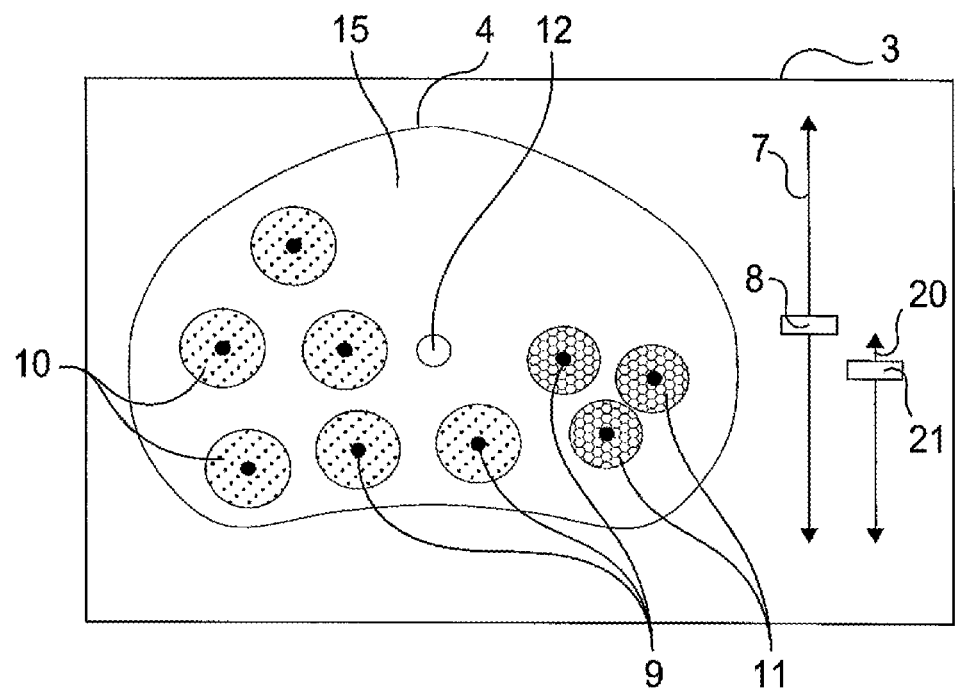
FIG. 3 is a schematic illustration of the image displayed by the display device shown in FIG. 2.
Figure 4:
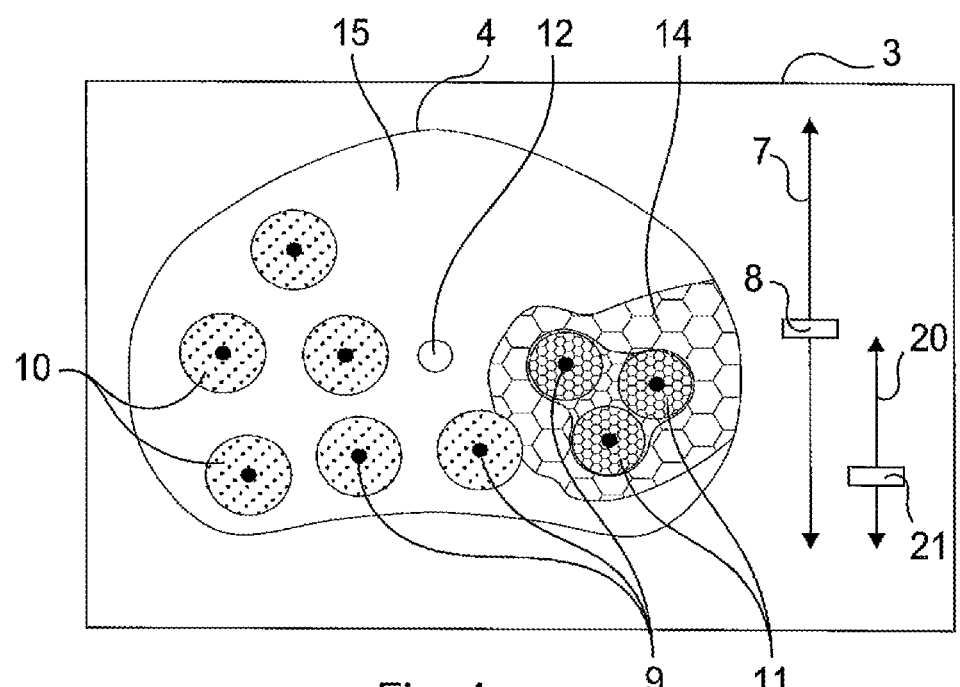
FIG. 4 is a schematic illustration of the image displayed by the display device shown in FIG. 2 once a clinician has manipulated the available cursors.

Referring to FIGS. 2 to 4, the display device according to the first embodiment of the invention is here intended to be used to visualize a prostate of a patient.

Of course, this use is not limiting, and it will be possible to use the visualization device on other internal organs of the patient, for example the liver, a kidney, a uterus, etc.

The device here comprises a computer system 1 incorporating a computer 2 and a screen 3 connected to the computer in order to display an image of the prostate 4.

In particular, the device comprises several man-machine interfaces, namely the keyboard 5 and the computer mouse 6.

The computer 2 is typically arranged to project a three-dimensional image of the prostate 4 on the screen 3. Preferably, the three-dimensional image of the prostate 4 is cut into a plurality of two-dimensional sectional images of the prostate, the clinician being able to use the man-machine interface 5, 6 to call up the display of the three-dimensional image or one of the two-dimensional images.

In particular, the computer 2 is arranged in such a way that, at the same time as displaying the images of the prostate 4, the screen 3 displays a line 7 provided with a cursor 8. By moving the cursor 8 on this line 7, for example with the aid of the mouse 6, the clinician changes the display from a two-dimensional image to another two-dimensional image. For example, the cursor 8 is vertical and is arranged such that the more the clinician moves the cursor 8 downward, the more the two-dimensional image displayed represents a lower part of the prostate 4, and conversely.

The computer is arranged to display, on the different images of the prostate 4, different portions 9 (only one is labeled here) of the prostate 4 that have been punctured when samples were taken earlier from the prostate for a study of said samples.

Preferably, the computer 2 is additionally arranged to display the different portions 9 in different colors depending on whether the result of the analysis of each sample is positive or negative. For example, the portions 9 where a disease has been detected are displayed in dark red, and the portions where a disease has not been detected are displayed in dark green.

Alternatively, instead of a two-color display (positive or negative result), the computer is arranged to display the different portions 9 in different colors depending on whether the result of the analysis of each sample is positive or negative and depending on the level of criticality (severity of the detected disease and/or propensity of said disease to develop, that is to say possible evolution of the disease) in the sample concerned and/or a surrounding sample. For example, the portions 9 where a disease has not been detected are displayed in a uniformly dark green color, and the portions where a disease has been detected are in a dark red that varies depending on the criticality.

The computer 2 is also arranged here to determine, on the basis of said samples, three-dimensional confidence zones 10 (only some of which are labeled here) and three-dimensional affected zones 11 of the prostate and to display, on the different images, said confidence zones 10 and said affected zones 11. The confidence zones 10 and the affected zones 11 are here defined so as to encompass, respectively, one of the previously punctured zones of the prostate for which no disease has been detected (for the confidence zones 10) and one of the previously punctured zones of the prostate for which a disease has been detected (for the affected zones 11). The confidence zones 10 and the affected zones 11 are here defined in such a way as to be centered around the corresponding sampled portion, totally encompassing the portion concerned.

This allows the clinician to visualize the situation by simultaneously displaying the punctured portions 9 and the state of the surrounding tissues. In this way, the clinician can more easily make a diagnosis and assess and plan how to treat the patient.

Particularly, the affected zones 11 and/or the confidence zones 10 are defined in such a way that their dimensions vary with the level of criticality detected in the associated sample and/or in the one or more neighboring samples.

Preferably, the computer 2 is additionally arranged to display the confidence zones 10 and the affected zones 11 in different colors. To this end, the computer 2 respects the color code associated with the portions 9 that have been punctured. The confidence zones 10 are therefore in green here, and the affected zones 11 in red.

This allows the clinician to better visualize the situation.

In particular, the computer 2 is here configured to display the confidence zones 10 and the affected zones 11 according to a color gradient, depending on the distance from the associated sampled portion 9 and on the criticality of the disease possibly detected in said portion 9.

Typically, the confidence zones 10 are of a lighter green than the associated sampled portion 9 and of a green that becomes increasingly lighter as the distance from said portion 9 increases. The affected zones 11 are of a red that is as dark as the corresponding sampled portion 9 in the case of a very high risk of cancer (for example in the case of TNM stage T4 N0 M0 or in the case of Gleason grade G8 or in the case of "high risk" on the D'Amico classification), and the affected zones 11 are of a lighter red than the associated sampled portion 9 and of a red that becomes increasingly lighter as the distance from said portion 9 increases in the other cases of classification of the detected disease.

Preferably, the computer 2 is additionally configured so as to display, on the different images of the prostate 4, one or more zones of the prostate that are to be preserved where possible by treatment. For example, the different images of the prostate 4 here comprise a representation of the urethra as the zone to be preserved.

This allows the clinician to better visualize the structures, tissues and organs to be preserved, so as to minimize the post-operative sequelae and the risks of secondary treatment for improving the efficacy of the treatment.

The zones to be preserved 12 are here represented in a different color than the confidence zones 10 and affected zones 11 and the associated portions 9. For example, the zones to be preserved 12 are displayed in blue.

The remainder of the images of the prostate 4 is shown in a different color than the confidence zones 10 and affected zones 11, the associated portions 9 and the zones to be preserved 12, or it is not colored.

A use of the device will now be described.

Firstly, the clinician supplies the computer 2 with the results of the samples that were taken (for example the classification of the different samples on the Gleason, D'Amico or TNM scales). It will be noted that the clinician is able to modify these results (or supply other supplementary data to complement these results) depending on his experience and/or on the results from other medical examinations, for example medical imaging procedures. The device thus allows the clinician flexibility in the generation of the images displayed.

Typically, the clinician enters these sampling data and/or supplementary data with the aid of the keyboard 5 and the mouse 6.

The computer 2 then determines the different volumes forming the confidence zone 10 or affected zone 11 around the portions where the biopsies have been performed.

Typically, for each affected zone 11, the computer defines the volume around a portion 9 where a biopsy has been performed by multiplying the volume of said portion 9 by a predetermined fixed percentage and by a variable factor calculated according to the criticality (severity of the detected disease and/or propensity of said disease to develop) of a disease detected on said sample (and optionally also on the neighboring samples).

Thus, more important affected zones 11 around the critical sampled portions 9 are displayed (for example in the case of TNM stage T4 N0 M0 or in the case of Gleason grade G8 or in the case of "high risk" on the D'Amico classification).

In a variant, it will also be possible, additionally or alternatively, to have a computer configured such that, for each confidence zone 10, the computer 2 defines the volume around a portion 9 where a biopsy has been performed by multiplying the volume of said portion 9 by a predetermined fixed percentage and by a variable factor calculated according to the criticality, for example, of a disease detected on the neighboring samples.

Moreover, the computer 2 also determines the different volumes forming zones to be preserved 12, for example with the aid of anatomical models.

The computer then determines the colors for displaying the different punctured portions 9 and the confidence zones 10, affected zones 11 and zones to be preserved 12.

The computer 2 is moreover configured to manage the intersections between the confidence zones and healthy zones when two samples are close.

Preferably, if a confidence zone 10 and an affected zone 11 intersect, the affected zone 11 outranks and completely replaces the associated confidence zone. Thus, the dimensions of the affected zone 11 will be greater than those of the associated confidence zone 10. Moreover, the colors of the affected zone 11 will therefore replace those of the confidence zone 10.

If two affected zones 11 intersect, it is the colors symbolizing the greater level of severity (distance closest to the sampling site and criticality of said sample) that predominate.

If two confidence zones 10 intersect, it is the colors symbolizing the clearest assumption of healthy tissue (distance from the sampling site) that predominate.

In the following step, the computer 2 displays three-dimensional images of the prostate 4, with the confidence zones 10, affected zones 11 and zones to be preserved 12 inserted in these images according to the abovementioned color code.

Preferably, once the images have been displayed, the clinician can additionally use the man-machine interfaces to effect:

a modification of the dimensions of the confidence zones 10 and/or affected zones 11, and/or a modification of the color code of the punctured portions, and/or a modification of the color code of the zones to be preserved 12, and/or a modification of the color code of the confidence zones 10, and/or a modification of the color code of the affected zones 11.

This therefore allows the clinician to adapt the displayed images so that they are as representative as possible of the actual situation, by virtue of the experience of the clinician who is also able to access other data such as medical images from radiology.

In this way, the volume around a portion 9 where a sample has been taken is defined in a predetermined manner by the computer 2 while being able to be modified by the clinician himself.

In particular, the computer 2 is additionally configured to be able to display a diseased general part 14 encompassing the various affected zones 11.

The computer 2 thus makes it possible to display the borders between the parts of the prostate that are estimated to be diseased, which further assists the work of the clinician.

Preferably, the computer 2 is additionally arranged to display the general part 14 in color. To this end, the computer 2 respects the color code associated with the portions which have been punctured and for which a disease has been detected. The diseased general part 14 is therefore in red here.

This allows the clinician to better visualize the situation.

In particular, the computer 2 is here configured to display the diseased general part 14 according to a color gradient depending on the distance separating the various affected zones 11 and on the criticality of the disease detected in the associated portions.

Typically, the diseased general part 14 is in a dark red between the affected zones 11, comprising at least one affected zone 11 associated with a sample noted with a very high risk of cancer (for example in the case of TNM stage T4 N0 M0 or in the case of Gleason grade G8 or in the case of "high risk" on the D'Amico classification), and the diseased general part is in a lighter red for the rest of the diseased general part 14.

The dimensions and/or the color code of the diseased general part 14 can be modified by the clinician via the man-machine interfaces.

In particular, the computer 2 is arranged such that the screen 3 displays, at the same time as the images of the prostate 4, a second line 20 provided with a second cursor 21. By moving the second cursor 21 on this second line 20, for example with the aid of the mouse 6, the clinician gradually enlarges the general part 14 from a display without the diseased general part 14 (corresponding to FIG. 3) as far as maximum dimensions defined by the computer 2. For example, the second cursor 21 is vertical and arranged such that the more the clinician moves the second cursor 21 downward, the greater the dimensions of the general part 14 become, and vice versa.

This therefore allows the clinician to adapt the diseased general part so that the displayed images are as representative as possible of the reality, by virtue of the experience of the clinician who is also able to access other data such as medical images from radiology. This in particular allows the clinician to better integrate the volume that is to be treated.

It will thus be seen that the displayed images are personalized for each patient, whether or not the clinician works on the images once they have been generated by the computer 2.

This allows the clinician to better estimate the appropriate treatment.

In particular, the computer 2 is configured such that the images displayed and realized with the aid of the computer can be exported to an external peripheral. Such a peripheral is, for example, a processor or any other peripheral that requires information contained in said images.

To this end, the computer 2 here uses a standard exchange model to transfer the images: by way of example, and only by way of example, an exchange model according to the DICOM standard (Digital Imaging and COmmunications in Medicine).

An example of the creation of the affected zones 11 and confidence zones 10 will follow below.

In the present case, it is assumed that the predictive power of the sampling follows a normal distribution as a function of the distance from the sampling. The law of decreasing reliability of the information as a function of the distance from the sampling is thus modelized with a Gaussian function.

For the remainder of the text, we adopt the following notation:

$\Omega$ The whole of a reference volume under consideration, $\Omega \in R^3$ (three-dimensional space of real numbers), $\Omega$ is a measurable space;

$C_n$ Biopsy core (that is to say the samples) of index n, n $\in$ N (all of the natural integers);

$V_n$ Subvolume of $\Omega$ (graphic representation) corresponding to the core $C_n$ n $\in$ N and corresponding also to a sampled portion 9;

X Point in space of the whole $\Omega$;

$P^n$ (X)Probability of the point X belonging to the volume $V_n$; belonging defines the probability of considering this point X as having the same properties as the biopsy core $C_n$ (in terms of probabilities).

Moreover, in the remainder of the text, we adopt the following definitions:

Representation volume

A representation volume corresponds to any volume belonging to $\Omega$ and defines confidence zones, affected zones.

Moreover, a geometric shape is also chosen representing the volume around the core $C_n$ as regards the confidence zones and the affected zones. For example, a cylinder is chosen here.

Gaussian function

As indicated above, we define $P^n$ (X) with the aid of a normal law having probability density:

$$f(d; \mu, \sigma) = \frac{1}{\sigma\sqrt{2\pi}} e^{-\frac{1}{2}\left(\frac{d-\mu}{\sigma}\right)^2}$$

where d corresponds to the minimum distance of X from the sampling n, $\mu$ is the expectation, $\sigma$ is the standard deviation of the law, and x is a real number.

Typically, the parameters $\mu$ and $\sigma$ are determined here from the results of the biopsy (and possibly the results of other medical examinations, for example visual scores attributed to suspect zones that were detected during medical imaging, or other results or scores), such that these parameters are thus specific to each patient.

In this way, the confidence zones and the affected zones are determined here not only from the analysis of the samples taken but also on the basis of a statistical approach to the presence of healthy or diseased tissue around the samples taken (here with the Gaussian function giving a probability density).

For example, for a confidence zone around a core of one centimeter, a normal law X~N(0.1) will be used. For an affected zone with a very high probability, high probability, low probability, very low probability around a core of one centimeter, use will be made, respectively, of a normal law X~N(0.1), X~N(0.75), X~N(0.25), X~N(0.0). The greater the chosen standard deviation, the more the representation volume will spread out.

These parameters are moreover modifiable by the clinician, who can thus use his experience or other results to modulate the confidence zones and the affected zones.

Preferably, these parameters are independent for each core $C_n$ considered. The definitions of said Gaussian parameters thus make it possible to attribute several types of Gaussian function f, hence several types of probabilities, to the different cores. Taking the example of a cancer detected in certain cores with a very high D'Amico score (high likelihood of spreading), the clinician will then be able to choose to apply a very high standard deviation for the cores concerned.

The aforementioned Gaussian function f is used to define the probability of a point X having the same properties as the next core $C_n$. Our variable d therefore designates the distance between X and the nearest point of the core $C_n$.

For example, this distance d is a Euclidian distance. The distance d is then preferably taken perpendicular to the cylindrical core $C_n$.

This distance d applied to the Gaussian function f gives us a lower probability (of the presence or absence of disease) as the distance from the core $C_n$ increases.

From a graphic point of view, this is simulated by a gradient of colors of they kind we have already explained. In particular, if the standard deviation σ chosen corresponds to three times the radius of the cylinder presented, the cylinder will be presented in a single color and not with a gradient of colors.

In the present case, it is also necessary for all of the calculated zones to be taken into account in order to control the union, disjoint union, intersection or else inclusion of the different zones among each other. In these different cases, it is in fact necessary to be able to adapt the gradient of colors to the size of each of the cores $C_n$ involved.

In the case where two zones of the same type overlap (two affected zones or two confidence zones), the probability used is to conserve the local maximum for each discrete spatial point used (pixel, metric unit, cell) for the confidence zones and also the affected zones.

$$\{P_{A \cup B}(X) = \max\{P^A(X), P^B(X)\}, \text{ if confidence zones or affected zones.}$$

In the case where two zones of a different type overlap, this gives the following:

For an overlap between a confidence zone (A) and an affected zone:

$$\begin{cases} P_{A \cap B}(X) = P^B(X), & \text{if } P^B(X) > \alpha \\ P_{A \cap B}(X) = \max\{P^A(X), P^B(X)\}, & \text{if not} \end{cases}$$

where α designates a predetermined threshold value modifiable by the clinician α E [0.1]. This value is given empirically or can be deduced from histological information supported by inputs for the algorithm (size of the cylinder, probability, Gaussian function). If α is chosen equal to 0, only the volume B is considered for the subset belonging to A and B.

For an overlap between a zone without diagnostic information (A) and any other volume (B)

$$P_{A \cap B}(X) = P^B(X)$$

Figure 5:
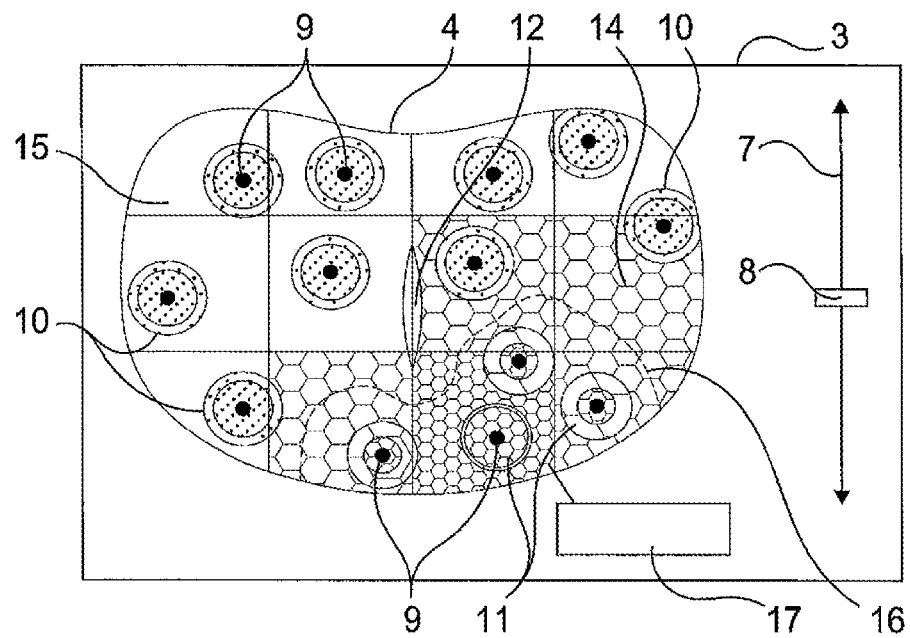
FIG. 5 is a schematic illustration of the image displayed by a display device according to a second embodiment of the invention.

Referring to FIG. 5, the second embodiment of the invention is identical to the first embodiment of the invention, except that the computer 2 is additionally configured to partition the prostate into different elements 15 (only one being labeled here) and to display, on the images of the prostate 4, the partition formed by these different elements 15.

The prostate is partitioned in a "patient-specific" manner automatically. For example, the prostate is partitioned into twelve elements.

In this way, it is easier for the clinician to interpret the images and to discuss the situation with a colleague or the patient.

The elements have the shape of triangles or quadrangles, for example, although the partition can be provided in any other way, for example via segment planes, ellipsoids, functions, etc.).

Once the images are displayed, the clinician can preferably also use the man-machine interfaces to modify the partitioning of the prostate.

It is also preferable for the screen then also to display information 17, especially indications on each of the elements 15 of the partition, for example the number of the element and the volume of this element (these items of information are shown in FIG. 5 only for a single element). In particular, for each element of the partition, the screen displays an indication of the severity of the disease detected within this element 15 (when the element has a sampled portion that is diseased), for example "Gleason 5+4 (B11) and 4+3 (B13)" and "Cancer probability: very high" (according to the D'Amico classification).

This allows the clinician to better understand the situation.

The computer 2 is moreover configured to calculate and display a diseased general part 14 encompassing at least the various affected zones 11 and formed by one or more elements 15 of the partition.

The computer 2 thus makes it possible to display the border of that part of the prostate estimated to be diseased, by which it is possible to further assist the work of the clinician.

The diseased general part 14 is determined, for example, on the basis of a statistical approach to the presence of healthy or diseased tissue around the affected zones 11, the statistical approach being based here on the result of the samples taken from the different portions of the prostate. For example, the diseased general part 14 is formed of all the elements 15 of the partition that have a face in common with an element 15 of the partition comprising an affected zone 11 associated with a sample noted as having a very high risk of cancer (for example T4 N0 M0 in the case of the TNM staging system, or G8 in the case of the Gleason grading system, or "high risk" on the D'Amico classification) and by the element 15 concerned. The diseased general part 14 can thus encompass zones displayed as confidence zones on account of its structure made up of elements 15.

Once the images are displayed, the clinician can also preferably use the man-machine interfaces to modify the dimensions of the general part 14.

Preferably, the computer 2 is additionally configured to display the diseased general part using the color code associated with the portions that have been punctured. The diseased general part 14 is thus represented in red.

This allows the clinician to better visualize the situation.

In particular, the computer 2 is here configured to display the diseased general part 14 according to a color gradient depending on the distance separating the different zones and the level of criticality of the diseased detected in the associated portions.

Typically, the diseased general part 14 is in dark red at the area of its element 15 comprising an affected zone 11 associated with a sample noted as having a very high risk of cancer (for example T4 N0 M0 in the case of the TNM staging system, or G8 in the case of the Gleason grading system, or "high risk" on the D'Amico classification), and the diseased general part 14 is in a lighter red for the rest of the diseased general part 14.

In particular, the computer 2 is moreover configured to display, on the images of the prostate 4, a zone detected as suspect 16 during a previous medical examination other than the biopsies, for example during MRI or during PET imaging (positron emission tomography). Only the edges of the zone 16 detected as suspect are typically displayed, for example by dotted lines.

It will thus be seen that the images displayed are personalized for each patient, whether or not the clinician works on the images once they have been generated by the computer 2.

This allows the clinician to better estimate the appropriate treatment.

In particular, the computer is configured such that the images displayed and realized with the aid of the computer can be exported to an external peripheral. Such a peripheral is, for example, a processor or any other peripheral that requires information contained in said images.

To this end, the computer 2 here uses a standard exchange model to transfer the images: by way of example, and only by way of example, an exchange model according to the DICOM standard (Digital Imaging and COmmunications in Medicine).

Figure 6:
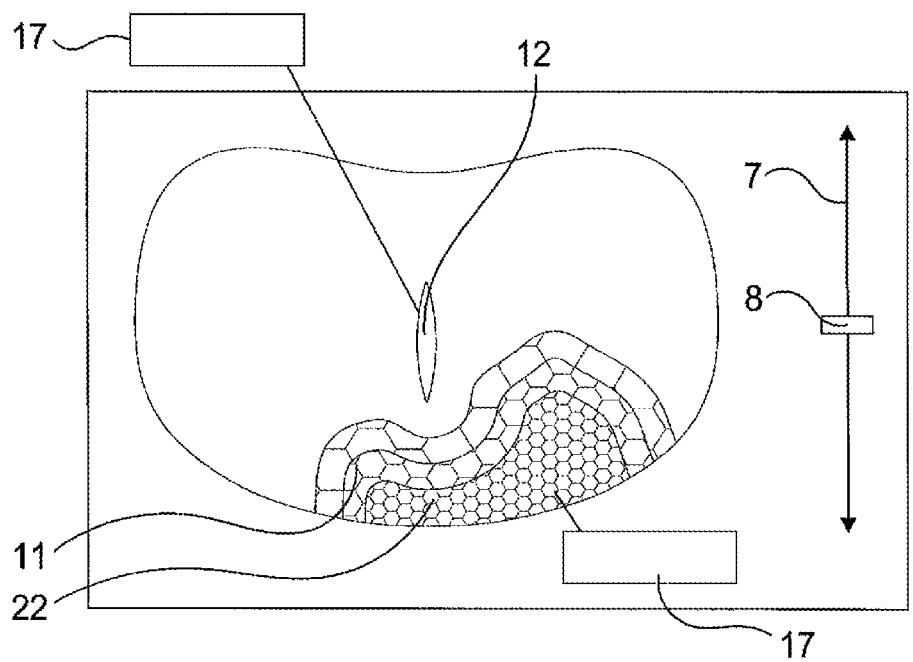
FIG. 6 is a schematic illustration of the image displayed by a display device according to a third embodiment of the invention.

Referring to FIG. 6, the third embodiment of the invention is identical to the first embodiment of the invention, except that the medical examination performed beforehand on the prostate involves medical imaging (for example MRI or PET).

The computer 2 is thus arranged to display, on the different images of the prostate 4, one or more suspect zones 22 detected during the medical imaging. In the present case, a single suspect zone has been detected.

This suspect zone is represented, for example, with the aid of algorithms for semi-automatic contour detection, with possible manual adjustment.

Preferably, the computer 2 is additionally arranged to display the suspect zone 22 in color. The colored zone is in dark red, for example.

The computer 2 is here also arranged to determine, from said suspect zone 22, a three-dimensional affected zone 11 of the prostate and to display said affected zone 11 on the different images. The affected zone 11 is here defined so as to encompass the suspect zone 22. The affected zone 11 is here defined so as to be centered around the suspect zone 22.

By way of example, for a mesh representing the suspect zone 22 with concave local portions, the shortest distance of the point X from each associated facet of the mesh can be used to determine the extrapolation distance d(ext).

Alternatively, the suspect zone 22 can be defined on the basis of the analysis of the score previously given to said suspect zone 22 (for example with the aid of the PI-RADS scale or the Likert scale) and also a statistical approach to the presence of healthy or diseased tissues around said suspect zone (for example by way of a Gaussian function giving a probability density with a fixed percentage and a variable percentage as in the first embodiment).

Preferably, the computer 2 is additionally arranged to display the affected zone in color. To this end, the computer 2 uses the color code associated with the suspect zone 22. The affected zone 11 is therefore in red.

This allows the clinician to better visualize the situation.

In particular, the computer 2 is configured to display the affected zone 11 according to a color gradient depending on the distance from the associated suspect zone 22.

Preferably, the computer 2 is additionally configured so as to display, on the different images of the prostate 4, one or more zones of the prostate that are to be preserved where possible by treatment. For example, the different images of the prostate 4 here comprise a representation of the urethra as the zone to be preserved 12.

This allows the clinician to better visualize the structures, tissues and organs to be preserved, so as to minimize the post-operative sequelae.

The zones to be preserved 12 are here represented in a different color than the affected zone 11 and the suspect zone 22. For example, the zones to be preserved 12 are displayed in blue.

The remainder of the images of the prostate 4 is shown in a different color than the affected zone 11, the suspect zone 22 and the zones to be preserved 12, or it is not colored.

Preferably, once the images have been displayed, the clinician can additionally use the man-machine interfaces to effect a modification:
of the dimensions of the suspect zone 22,
and/or of the dimensions of the affected zone 11,
and/or a modification of the color code of the suspect zone 22,
and/or a modification of the color code of the affected zone 11,
and/or a modification of the color code of the zones to be preserved 12.

This therefore allows the clinician to adapt the displayed images so that they are as representative as possible of the actual situation, by virtue of the experience of the clinician who is also able to access other data such as biopsy data, for example.

It is also preferable that the computer 2 is arranged to display, on the screen, items of information 17 that indicate the name and volume of the zone to be preserved (for example "urethra 1 cm$^3$") or else the volume of the suspect zone, and also a probability of cancer of said zone (for example "8 cm$^3$, Probability of cancer: high").

This allows the clinician to better understand the situation.

It will thus be seen that the displayed images are personalized for each patient, whether or not the clinician works on the images once they have been generated by the computer 2.

This allows the clinician to better estimate the appropriate treatment.

In particular, the computer 2 is configured such that the images displayed and realized with the aid of the computer can be exported to an external peripheral. Such a peripheral is, for example, a processor or any other peripheral that requires information contained in said images.

To this end, the computer 2 here uses a standard exchange model to transfer the images: by way of example, and only by way of example, an exchange model according to the DICOM standard (Digital Imaging and COmmunications in Medicine).

The invention is not limited to what has been described above, and instead it encompasses any variant falling within the scope defined by the claims.

It will be possible for the device to comprise a different number of man-machine interfaces. The one or more man-machine interfaces can be different than those cited, for example a touch screen, a control unit comprising buttons, a stylus, etc.).

Although the computer here makes it possible to display a three-dimensional image of the internal organ and at the same time two-dimensional section planes of the internal organ, it will also be possible for the computer to be arranged to project only the three-dimensional image or only the two-dimensional section planes of the internal organ (thus forming a three-dimensional study of the internal organ) or to project only one or more two-dimensional section planes. Moreover, although the three-dimensional image is here cut into a plurality of two-dimensional sectional images of the prostate according to a section plane having the cranial/caudal axis as its normal, it will be possible for the three-dimensional image to be cut in two-dimensional planes according to other section axes, for example the anterior/posterior axis or the transverse axis. For example, the computer will be able to display both the three-dimensional image of the internal organ and the three series of two-dimensional section planes of the internal organ that are defined according to the three aforementioned axes. The computer will thus be able to display a different cursor associated with each series of section planes, so that a clinician can move independently in each series of section planes.

Although the screen here displays one or more zones to be preserved, one or more confidence zones and one or more affected zones at the same time, it will be possible to display a different number of types of zones and in particular just affected zones or just confidence zones.

Although the different zones and/or general parts are always displayed together here, it will also be possible to display only the zones (in part or in full) and/or general parts. For example, a clinician will be able to use the man-machine interface to select what he wants to appear on the image.

Moreover, the computer will be able to be configured to display different items of information on the image. For example, each affected zone and/or confidence zone and/or zone to be preserved will be able to be numbered. It will be possible to attribute metric indications to one, several or all of the zones. It will be possible to insert items of information on the level of criticality (severity of the detected disease and/or propensity of said disease to develop) of the diseases detected in the sampled portions and/or in the zone under consideration. It will be possible to add clinical information to the image, for example by inserting a representation of zones palpated by the clinician, suspect zones detected by examinations other than the biopsy. It will be possible to display the volume of a zone, the volume of a puncture passing through several zones, information on surface and distance, visual assessments made by the clinician, etc.

The confidence zones and/or affected zones will be able to be defined from the results of analyses and/or by a statistical approach, for example based on clinical studies, statistical distribution charts, distribution models (thus allowing an organ to be partitioned into different elements and to assign one or more elements to a confidence zone and/or an affected zone) and/or optimal distribution models (moreover making it possible for the elements adjacent to elements already assigned to an affected zone to be assigned to said affected zone), probabilities of disease depending on the position of suspect zones or diseased samples in the internal organ, statistical functions, etc. It will be noted that the statistical approach is personalized to each patient on account of the fact that it is based on at least one portion of the internal organ from which at least one sample has been taken and/or to the zone previously identified as suspect during the medical imaging, so as to define the confidence zones and/or affected zones. In the case of a partitioning of the internal organ, the confidence zones and/or affected zones will thus be able to be directly formed by one or more elements of the partitioning. Complementary to this, the clinician will be able to modify the volumes or the surfaces of the confidence zones and/or affected zones and/or zones to be preserved and/or general parts in accordance with what has been calculated and displayed by the device. This will make it possible to adapt still further the calculations to the specific case of the patient according to the experience possessed by the clinician. For example, in the case of a partitioning of the organ where only the elements forming or comprising a confidence zone and/or affected zone are highlighted (for example with a particular color) in relation to other elements, the clinician will be able to use a man-machine interface to request that the elements having a surface in common with said elements are also highlighted, so as to increase the dimensions of the affected zones and/or confidence zones and/or one or more general parts.

As regards the representation, although the confidence zones, the affected zones and the diseased general part are here represented in a color gradient, other types of representation may be envisioned, for example binary representation (either colored or uncolored) or a transparency gradient (zones that are more opaque or less opaque depending on the level of criticality of the disease that is detected).

Moreover, instead of displaying the general parts by colors and borders, it will be possible for the general parts to be displayed differently, for example in partition form by displaying the ridges of the partition elements and/or the faces of said elements. Similarly, the confidence zones and/or affected zones and/or confidence zones will be able to be displayed differently, for example in partition form by displaying the ridges of the elements of the partition and/or the faces of said elements.

Although a normal law has been chosen in the algorithm described, it will be possible to choose any other type of law in order to define the confidence zones and/or affected zones. It will also be possible to choose laws of a different type depending on the zones to be defined. The applicable laws will be, for example, of the exponential, logarithmic or else linear type. It is also conceivable to use purely probabilistic laws, for example based on Bayes' theorem. These probabilistic laws make it possible to deduce the a posteriori probability of the presence or absence of a disease from its a priori probability and the observations made during the analysis of the samples, as a function of the distance to the information.

Alternatively or as a complement, the affected zones and/or confidence zones will be able to be defined as a function of the measurement error possibly made by the device and/or the apparatus involved in the medical examination previously carried out on the internal organ. For example, if the medical examination is a medical imaging procedure, the apparatus that permitted this imaging will generate an image with an error, and a suspect zone will be detected with an error on its location, which error will be used in the calculations to determine an affected zone. Similarly, if the examination is a biopsy, the place where the biopsy will be displayed on an image will be able to be offset from the place where the biopsy has actually been actually performed. In this way, if a biopsy core contained cancerous cells, said cells would be able to be derived from a zone actually offset by 1 millimeter from the zone displayed on the screen as supposedly that of the biopsy.

By integrating these errors in the calculation of the affected zones and/or confidence zones, it will thus be possible to obtain affected zones and/or confidence zones that are more representative of reality. For example, the computer of the device according to a particular embodiment of the invention will be able to be configured to automatically take the errors of the device itself and/or of the apparatus that permitted the previous medical examination (biopsy and/or medical imaging) into consideration in its calculation of the affected zone and/or confidence zone. For the previous medical examination, the error will depend generally on the type of imaging used and/or on the type of realignment (for example elastic or rigid) used (for the biopsy, as for the medical imaging, an image is in fact conserved during a biopsy in order to be able to study where the biopsy was performed in the internal organ). Of course, the computer will be configured to cumulate, if so desired, the different errors in its calculation of the affected zone and/or confidence zone (there may in fact be an accumulation of errors, for example in the case of multiple realignment).

The device according to a particular embodiment of the invention will thus be able to be configured to recover, from a data base, the errors associated with each type of imaging and with each type of realignment and to calculate the confidence zones and/or affected zones, for example once the practitioner has indicated the type of imaging and the type of realignment that are used. For example, for an elastic realignment, the error will be considered as being + or − one millimeter or + or −2 millimeters; for imaging of the MRI type, it will be considered as being + or −5 millimeters; for imaging of the ultrasound type, it will be considered as being + or −1 millimeter.

It will also be possible to take into account the fact that the errors may be different depending on the measurement axes of the device and/or the apparatus having been involved in the medical examination previously carried out on the internal organ. For example, if the medical examination is a medical imaging procedure of the MRI type, the apparatus that permitted this imaging procedure will generate an image with a different error on one of its three axes in relation to its two other axes, since the resolution on one of its axes will typically be 3 millimeters, whereas it will be 0.7 millimeter on the two other axes.

Moreover, although the distance "d" chosen in the algorithm is here a Euclidian distance, it will be possible to choose other types of distances, for example an average distance from the sampling, or else Chebyshev's distance. In fact, knowing the size of each pixel forming the displayed image, it is possible to define a Chebyshev metric joining each spatial point to a core Cn in a pixelated space. Chebyshev's distance can advantageously be used to define a distance at cell level. Based on this, it would also be possible to employ Moore's concept of neighborhood used in cell biology by defining a Moore vicinity of the order N for each cell, or group of cells, of a core $C_n$. Although each core in the described algorithm has been considered as a single element, a core $C_n$ will be able to be subdivided into a set of k "fragments" of cores defined as $C_n^k$. The algorithm will then be applied to the elements $C_n^k$.

Of course, the different embodiments described in the present application will be able to be combined. For example, the device of the first embodiment will be able to be configured to display information as in the second embodiment and in the third embodiment. Generally, for the different embodiments, these items of information will be able to comprise, for example, an indication of the criticality of the disease detected within each sample, indications concerning the volume of the samples, indications concerning the volume of the affected zones, confidence zones, zones to be preserved, concerning a suspect zone, etc. In the same way, the device of the first embodiment will be able to be configured to display, on the images, a zone detected as suspect during a previous medical examination, as in the second embodiment. It will also be possible to combine the first embodiment or the second embodiment with the third embodiment, that is to say to display on the images confidence zones and/or affected zones associated with samples carried out and at the same time affected zones associated with a zone identified as suspect during a previous examination by medical imaging. It will thus advantageously be possible to benefit from the complementary nature of the information between the medical examinations of the biopsy type and the medical examinations of the medical imaging type. In the case of the third embodiment with several suspect zones represented (and the corresponding affected zones), it will be possible, as in the first embodiment or the second embodiment, to have the device configured to define and display a diseased general part surrounding the different suspect zones (and modifiable by the clinician). The partitioning of the internal organ into different elements will be able to be applied to any embodiment described.

The invention claimed is:

1. A device for visualizing an internal organ of a patient, comprising a computer and a screen connected to the computer in order to display at least one image of the internal organ, wherein the computer is configured:

to determine, from at least one medical examination previously carried out on the internal organ, at least one confidence zone and/or at least one affected zone, at least partially encompassing one or more portions of the internal organ where samples have been taken and/or at least partially encompassing one or more zones previously identified as suspect during a medical imaging procedure, the determination being based on:

a statistical approach to the presence of healthy or diseased tissues around a portion of the internal organ where at least one sample has been taken and/or around a zone previously identified as suspect during the medical imaging procedure;

and/or on an analysis of the samples taken:

to display, on the screen, the image of the internal organ supplemented with the confidence zone and/or the affected zone.

2. The device as claimed in claim 1, in which the computer is arranged to project a three-dimensional image of the internal organ on the screen.

3. The device as claimed in claim 1, in which the computer is arranged to project two-dimensional sectional images of the internal organ.

4. The device as claimed in claim 1, in which the computer is arranged to display, on the image of the internal organ, at least one portion of the internal organ that has been punctured during the sampling procedures.

5. The device as claimed in claim 4, in which the confidence zone and/or affected zone completely encompasses said portion.

6. The device as claimed in claim 4, in which the confidence zone and/or the affected zone is displayed on the screen with a color gradient depending on the distance from the associated sampled portion and/or on the criticality of the disease possibly detected in said portion.

7. The device as claimed in claim 1, in which the confidence zone and the affected zone are not displayed in the same color.

8. The device as claimed in claim 1, in which the computer is configured in such a way as to display, on the image of the internal organ, at least one zone of the internal organ that is to be preserved.

9. The device as claimed in claim 1, in which the computer is additionally configured to partition the internal organ into different elements and to display, on the image of the internal organ, the partition formed by these different elements.

10. The device as claimed in claim 9, in which the confidence zone and/or the affected zone is formed by one or more elements.

11. The device as claimed in claim 1, in which the computer is configured in such a way as to display, on the image of the internal organ, at least one item of information associated with the confidence zone and/or the affected zone.

12. The device as claimed in claim 1, in which the computer is configured to be able to display a diseased general part encompassing at least some of the various affected zones.

13. The device as claimed in claim 1, in which the computer is configured in such a way as to partition the internal organ into different elements and to display, on the image of the internal organ, the partition formed by these various elements, the computer additionally being configured in such a way as to display a diseased general part encompassing at least one element of the partition comprising one or more affected zones.

14. The device as claimed in claim 13, in which the computer is configured in such a way that the diseased general part also encompasses at least one element of the partition in contact with the element of the partition comprising one or more affected zones.

15. The device as claimed in claim 1, in which the computer is configured to export the displayed image to an external peripheral.

16. The device as claimed in claim 1, in which the computer is arranged to define the affected zone and/or confidence zone also with the aid of a measurement error of the apparatus that was involved in the medical examination performed beforehand on the internal organ.

17. A method for visualizing an internal organ of a patient with the aid of a device according to claim 1, comprising the step of determining the one or more confidence zones and/or affected zones and of displaying said one or more zones.

18. A device for visualizing an internal organ of a patient, comprising a computer and a screen connected to the computer in order to display at least one image of the internal organ, wherein the computer is configured:
to determine, from at least one medical examination previously carried out on the internal organ, at least one confidence zone and/or at least one affected zone, at least partially encompassing one or more portions of the internal organ where samples have been taken and/or at least partially encompassing one or more zones previously identified as suspect during a medical imaging procedure, the determination being based on:
a statistical approach to the presence of healthy or diseased tissues around a portion of the internal organ where at least one sample has been taken and/or around a zone previously identified as suspect during the medical imaging procedure;
and/or on an analysis of the samples taken:
to display, on the screen, the image of the internal organ supplemented with the confidence zone and/or the affected zone,
wherein the confidence zone and/or the affected zone is displayed on the screen with a color gradient depending on the distance from the associated sampled portion and/or on the criticality of the disease possibly detected in said portion.

19. A device for visualizing an internal organ of a patient which allows the clinician to better estimate the appropriate treatment, comprising a computer and a screen connected to the computer in order to display at least one image of the internal organ, the computer configured:
to determine, from at least one medical examination previously carried out on the internal organ, at least one confidence zone and/or at least one affected zone, at least partially encompassing one or more portions of the internal organ where samples have been taken and/or at least partially encompassing one or more zones of the internal organ previously identified as suspect during a medical imaging procedure, the determination being based on a statistical approach to the presence of healthy or diseased tissues around a portion of the internal organ where at least one sample has been taken and/or around a zone of the internal organ previously identified as suspect during the medical imaging procedure;
and/or on an analysis of the samples taken to display, on the screen, the image of the internal organ supplemented with the confidence zone and/or the affected zone.

20. A device for visualizing an internal organ of a patient which allows the clinician to better estimate the appropriate treatment, comprising a computer and a screen connected to the computer in order to display at least one image of the internal organ, the computer configured:
to determine, from at least one medical examination previously carried out on the internal organ, at least one confidence zone and/or at least one affected zone, at least partially encompassing one or more portions of the internal organ where samples have been taken and/or at least partially encompassing one or more zones of the internal organ previously identified as suspect during a medical imaging procedure, the determination being based on a statistical approach to the presence of healthy or diseased tissues around a portion of the internal organ where at least one sample has been taken and/or around a zone of the internal organ previously identified as suspect during the medical imaging procedure;
and/or on an analysis of the samples taken to display, on the screen, the image of the internal organ supplemented with the confidence zone and/or the affected zone;
wherein the device comprise at least one man-machine interface that permit to modify the dimensions of the confidence zone and/or the affected zone once the image has been displayed.

* * * * *